US008425935B2

(12) United States Patent
Kolter et al.

(10) Patent No.: US 8,425,935 B2
(45) Date of Patent: Apr. 23, 2013

(54) PHARMACEUTICAL FORMULATION FOR PRODUCING RAPIDLY DISINTEGRATING TABLETS

(75) Inventors: Karl Kolter, Limburgerhof (DE); Marcus Wichtner, Mannheim (DE); Michael Schönherr, Frankenthal (DE); Jan-Peter Mittwollen, Edingen-Neckarhausen (DE)

(73) Assignee: BASF SE, Ludwigshafen (DE)

( * ) Notice: Subject to any disclaimer, the term of this patent is extended or adjusted under 35 U.S.C. 154(b) by 74 days.

(21) Appl. No.: 12/158,236

(22) PCT Filed: Dec. 11, 2006

(86) PCT No.: PCT/EP2006/069515
§ 371 (c)(1),
(2), (4) Date: Jun. 19, 2008

(87) PCT Pub. No.: WO2007/071581
PCT Pub. Date: Jun. 28, 2007

(65) Prior Publication Data
US 2008/0299194 A1 Dec. 4, 2008

(30) Foreign Application Priority Data

Dec. 21, 2005 (EP) .................................... 05112654
Dec. 23, 2005 (EP) .................................... 05112969

(51) Int. Cl.
*A61K 9/14* (2006.01)
*A61K 47/36* (2006.01)
*A61K 9/20* (2006.01)

(52) U.S. Cl.
USPC .................. 424/465; 514/772.3; 424/489

(58) Field of Classification Search .............. 424/465, 424/489; 514/772.3
See application file for complete search history.

(56) References Cited

U.S. PATENT DOCUMENTS

| 4,087,360 | A  | * | 5/1978 | Faust et al. ................. 210/701 |
| 5,569,469 | A  | * | 10/1996 | Lovrecich .................... 424/501 |
| 6,495,177 | B1 | * | 12/2002 | deVries et al. ................ 426/72 |
| 6,696,085 | B2 |   | 2/2004 | Rault et al. |
| 7,572,390 | B2 | * | 8/2009 | Martin ..................... 252/186.33 |
| 2001/0010825 | A1 |   | 8/2001 | Shimizu et al. |
| 2002/0071864 | A1 |   | 6/2002 | Kim et al. |
| 2004/0058896 | A1 | * | 3/2004 | Dietrich et al. ............. 514/171 |
| 2004/0110661 | A1 | * | 6/2004 | Dietrich et al. ............... 514/1 |

FOREIGN PATENT DOCUMENTS

| EP | 0839526 A2 | 5/1998 |
| JP | 2004-265216 | 9/2004 |
| WO | WO-03/051388 A2 | 6/2003 |
| WO | WO-03/072084 A1 | 9/2003 |

OTHER PUBLICATIONS

See BASF, Accelerators—Kollidon CL, Kollidon CL-F, Kollidon CL-SF, Kollidon CL-M at http://www.basf-chemtrade.de/images/stories/broschueren/PHI/basf_kollidon_grades.pdf—accessed Nov. 23, 2009.*
"Agglomerate"—Dictionary.com, accessed May 31, 2012.*

* cited by examiner

*Primary Examiner* — Frederick Krass
*Assistant Examiner* — Adam C Milligan
(74) *Attorney, Agent, or Firm* — Novak Druce Connolly Bove + Quigg LLP

(57) ABSTRACT

A pharmaceutical formulation in the form of agglomerates comprising
a) 60-97% by weight of sugar or sugar alcohols,
b) 1-25% by weight of crosslinked polyvinylpyrrolidone,
c) 1-15% by weight of water-insoluble, film-forming polymers,
d) 0-15% by weight of water-soluble polymers and
e) 0-15% by weight of further pharmaceutically customary excipients,
the sum of the components a) to e) being 100% by weight.

17 Claims, No Drawings

PHARMACEUTICAL FORMULATION FOR PRODUCING RAPIDLY DISINTEGRATING TABLETS

RELATED APPLICATIONS

This application is a national stage application (under 35 U.S.C. §371) of PCT/EP2006/069515, filed Dec. 11, 2006, which claims benefit of European application 05112654.8, filed Dec. 21, 2005, and European application 05112969.0, filed Dec. 23, 2005.

The present invention relates to pharmaceutical formulations in the form of agglomerates for the preparation of rapidly disintegrating tablets, comprising sugar or sugar alcohols, crosslinked polyvinylpyrrolidone and water-insoluble polymers.

Tablets which disintegrate rapidly in the mouth and/or dissolve rapidly are becoming increasingly important for the oral application of medicaments. Such tablets must disintegrate within a short time, preferably within 30 seconds, in the oral cavity and have a pleasant taste and must not leave behind a gritty sensation. Furthermore they should be easy to produce, direct tabletting having considerable advantages over moist granulation, and should have high mechanical strength so that they withstand packaging procedures, transport and also pressing out from packaging without damage.

The products and processes described to date do not meet these requirements or do so only very inadequately.

Rapidly disintegrating tablets frequently consist of sugar and sugar alcohols, effervescent systems, microcrystalline cellulose and other water-insoluble fillers, calcium hydrogen phosphate, cellulose derivatives, cornstarch or polypeptides. Furthermore, water-soluble polymers, conventional disintegrants (crosslinked PVP, sodium and calcium salts of crosslinked carboxymethylcellulose, the sodium salt of carboxymethyl starch, hydroxypropylcellulose having a lower degree of substitution L-HPC) and substantially inorganic water-insoluble constituents (silicas, silicates, inorganic pigments) are used. Furthermore, the tablets may also comprise surfactants.

WO 2003/051338 describes a directly tablettable and readily compressible excipient formulation which comprises mannitol and sorbitol. First, an excipient premix is prepared by dissolution of mannitol and sorbitol in water and subsequent spray drying (customary spray drying and SBD method). Mannitol may also be added to this coprocessed mixture. Tablets which additionally comprise disintegrant, lubricant, pigment and an active substance should disintegrate within 60 seconds in the oral cavity.

US 2002/0071864 A1 describes a tablet which disintegrates within 60 seconds in the oral cavity and is mainly formulated from a physical mixture of spray-dried mannitol and a coarse-particled crosslinked polyvinylpyrrolidone and a limited selection of active substances. These tablets have a hardness of about 40 N and produce an unpleasant, gritty sensation in the mouth.

According to U.S. Pat. No. 6,696,085 B2 a methacrylic acid copolymer of type C is to be used as a disintegrant. The methacrylic acid copolymer of type C is a polymer which is resistant to gastric fluid and insoluble in the acidic pH range but water-soluble in the pH range of 7 as is present in the oral cavity. In addition to low hardness (<20 N), the tablets have high friability (>7%) and have a high proportion in the region of 15% by weight of a coarse-particled disintegrant. They consequently have low mechanical strength and, owing to the high proportion of coarse-particled disintegrant, produce an unpleasant, gritty sensation in the mouth.

EP 0839526 A2 describes a pharmaceutical dosage form consisting of an active substance, erythritol, crystalline cellulose and a disintegrant. Furthermore, mannitol is incorporated and crosslinked polyvinylpyrrolidone is used as a disintegrant, so that a physical mixture forms. The tablets are said to decompose within 60 seconds in the oral cavity.

The application JP 2004-265216 describes a tablet which disintegrates in the mouth within 60 seconds and consists of an active substance, a water-soluble polyvinyl alcohol/polyethylene glycol copolymer, sugar/sugar alcohol (mannitol) and disintegrant.

It was an object of the present invention to provide tablets which disintegrate rapidly in the mouth, leave behind a pleasant sensation in the mouth and are mechanically very stable.

Accordingly, a pharmaceutical formulation for the preparation of tablets which disintegrate rapidly in the mouth was found, which consists of agglomerates comprising a) 60-97% by weight of at least one sugar or sugar alcohol or mixtures thereof,
b) 1-25% by weight of a crosslinked polyvinylpyrrolidone,
c) 1-15% by weight of water-insoluble polymers,
d) 0-15% by weight of water-soluble polymers and
e) 0-15% by weight of further pharmaceutically customary excipients, the sum of the components a) to e) being 100% by weight.

Furthermore, a process for the preparation of such agglomerates was found.

Furthermore, tablets which disintegrate rapidly in the mouth and comprise such formulations were found. The tablets disintegrate in the mouth or in an aqueous medium within 40 seconds, preferably within 30 seconds, particularly preferably within 20 seconds.

The pharmaceutical formulations comprise, as component a), from 60 to 97% by weight, preferably from 70 to 95% by weight, particularly preferably from 75 to 93% by weight, of a sugar, sugar alcohol or mixtures thereof. Suitable sugars or sugar alcohols are trehalose, mannitol, erythritol, isomalt, maltitol, lactitol, xylitol and sorbitol. The sugar or sugar alcohol components are preferably finely divided, with mean particle sizes of from 5 to 100 µm. If desired, the particle sizes can be adjusted by milling. Mannitol, erythritol or mixtures thereof are preferably used.

Crosslinked polyvinylpyrrolidones in amounts of from 1 to 25% by weight, preferably from 2 to 15% by weight, particularly preferably from 3 to 10% by weight, are used as component b). Such crosslinked polyvinylpyrrolidones are water-insoluble but not film-forming. The crosslinked polyvinylpyrrolidone may have a mean particle size from 2 to 60 µm, preferably less than 50 µm, particularly preferably less than 30 µm. Crosslinked polyvinylpyrrolidones having a hydration capacity greater than 6.5 g/g are very particularly preferred. Here, the determination of the hydration capacity is effected by the following method:

2 g of polymer are weighed into a centrifuged tube and allowed to swell with 40 ml of water for 15 minutes. Thereafter, centrifuging is effected for 15 minutes at 2000 rpm and the supernatant liquid is poured off as completely as possible.

$$\text{Hydration capacity} = \frac{\text{Resulting weight} - \text{tare}}{\text{Weight taken}}$$

In the formulation, the high hydration capacity of the crosslinked polyvinylpyrrolidone leads to very rapid disintegration and gives a particularly soft sensation in the mouth.

Water-insoluble polymers in amounts of from 1 to 15% by weight, preferably from 1 to 10% by weight, are used as component c). These are polymers. Preferred polymers are those which are insoluble in the pH range from 1 to 14, i.e. have a water insolubility which is pH independent at every pH. However, polymers which are water-insoluble at any pH in the pH range from 6 to 14 are also suitable.

The polymers should be film-forming polymers. In this context, film-forming means that the polymers have a minimum film formation temperature of from −20+150° C., preferably from 0 to 100° C., in aqueous dispersion.

Suitable polymers are polyvinyl acetate, ethylcellulose, methyl methacrylate/ethyl acrylate copolymers, ethyl acrylate/methyl methacrylate/trimethylammoniumethyl methacrylate terpolymers. Butyl methacrylate/methyl methacrylate/dimethylaminoethyl methacrylate terpolymers.

The acrylate/methacrylate copolymers are described in more detail in the European Pharmacopoeia as Polyacrylate Dispersion 30%, in the USP as Ammonio Methacrylate Copolymer and in JPE as Aminoalkyl Methacrylate Copolymer E. Polyvinyl acetate is used as preferred component c). This may be used as an aqueous dispersion having solids contents of from 10 to 45% by weight. In addition, a preferred polyvinyl acetate is one having a molecular weight of from 100 000 to 1 000 000 dalton, particularly preferably from 200 000 to 800 000 dalton.

Furthermore, the formulations may comprise water-soluble polymers in amounts of from 0 to 15% by weight as component d). Suitable water-soluble polymers are, for example, polyvinylpyrrolidones, vinylpyrrolidone/vinyl acetate copolymers, polyvinyl alcohols, polyvinyl alcohol/polyethylene glycol graft copolymers, polyethylene glycols, ethylene glycol/propylene glycol block copolymers, hydroxypropylmethylcullulose, hydroxypropylcellulose, hydroxyethylcellulose, carrageenans, pectins, xanthans and alginates.

If desired, flavor and appearance of the tablets obtained from the formulations can be further improved by adding pharmaceutically customary excipients (component e)) in amounts of from 0 to 15% by weight, for example such as acidifying agents, buffer substances, sweeteners, flavors, flavor enhancers and colorants. The following substances are particularly suitable here: citric acid, tartaric acid, ascorbic acid, sodium dihydrogen phosphate, cyclamate, saccharin sodium, aspartame, menthol, peppermint flavor, fruit flavors, vanilla flavor, glutamate, riboflavin, beta-carotene, water-soluble colorants and finely divided colored lacquers. By adding thickeners, such as high molecular weight polysaccharides, the sensation in the mouth can be additionally improved by increasing the softness and the sensation of volume.

Furthermore, surfactants may also be added as components e). Suitable surfactants are, for example, sodium laurylsulfate, dioctyl sulfosuccinate, alkoxylated sorbitan esters, such as polysorbate 80, polyalkoxylated derivatives of castor oil or hydrogenated castor oil, for example Cremophor® RH 40, alkoxylated fatty acids, alkoxylated hydroxyl-fatty acids, alkoxylated fatty alcohols, alkali metal salts of fatty acids and lecithins.

Furthermore, finely divided pigments may also be added for further improvement of the disintegration, because they increase the internal interfaces and hence water can penetrate more rapidly into the tablet. These pigments, such as iron oxides, titanium dioxide, colloidal and precipitated silica, calcium carbonates or calcium phosphates, must of course be very finely divided since otherwise a grainy flavor once again results.

The preparation of the formulations according to the invention can be effected by pelletizing in mixers, fluidized-bed apparatuses or spray towers. Solid starting materials and granulating liquid are first mixed with one another and a moist mixed material is then dried. According to the present invention, the granulating liquid used is an aqueous dispersion of component c), of the water-insoluble polymer.

During the agglomeration in the fluidized bed, an aqueous dispersion of the water-insoluble polymer is sprayed onto a fluidized mixture of sugar or sugar alcohol and crosslinked PVP with the result that the fine particles agglomerate. The temperatures of the inlet air are from 30 to 100° C. and the temperatures of the waste air are from 20 to 70° C.

In the preparation in spray towers, the so-called FSD or SBD technology (FSD: fluidized spray drying; SBD: spray bed drying) is preferably used. Here, a solution of the sugar or sugar alcohol in water is first spray-dried and the addition of crosslinked PVP and the spraying in of an aqueous dispersion of the water-insoluble polymer are effected in the lower part of the spray dryer or in a connected fluidized bed, with the result that the particles agglomerate. Fine particles can furthermore be blown again in front of the spray nozzle of the sugar or sugar alcohol solution and additionally agglomerated. A procedure starting from the crystalline form of the sugar or sugar alcohol is also possible in the spray tower, FSD or SBD. The crystalline sugar or sugar alcohol is added at the top of the spray tower or in the recycle stream of fine material. By spraying an aqueous dispersion of the water-insoluble polymer, this crystalline solid is agglomerated in the tower.

It may prove advantageous for the agglomeration process to carry out a multistage spray process. At the beginning, the spray rate is kept low in order to prevent over-moistening of the initially taken product and hence adhesion thereof. With increasing duration of the process, the spray rate can be increased and thus the tendency to agglomerate can be raised. It is also possible to adapt the inlet air flow rate and/or temperature in an appropriate manner during the process. Particularly during the drying phase, it is advantageous to reduce the inlet air flow rate and hence to prevent abrasion of the agglomerates due to a high mechanical load.

The fineness of the spray droplet of the binder solution or dispersion (adjustable via the atomization gas pressure), the nozzle geometry and the distance from the nozzle to the product bed may be regarded as further adaptation parameters for the agglomerate size. The finer and more uniform the spraying, the finer and more uniform are the resulting agglomerates. The further away the nozzle is from the product bed, the poorer is the agglomeration behavior.

Furthermore, the agglomerates can also be produced in a mixer by continuous aggregation with mixing. Such a continuous form of aggregation with mixing is the so-called "Schugi granulation". There, solid starting materials and the granulating liquid comprising the water-insoluble polymer are thoroughly mixed with one another in a continuously operating vertically arranged high-speed mixer (cf. also M. Bohnet, "Mechanische Verfahrenstechnik", Wiley VCH Verlag, Weinheim 2004, page 198 et seq.).

According to a particular embodiment, the crosslinked PVP is suspended in the aqueous dispersion of the water-insoluble polymer.

The agglomerates thus obtained have a mean particle size of 100-600 μm, preferably 120-500 μm and particularly preferably 140-400 μm. The water-insoluble, film-forming polymer serves as an agglomerating agent for agglomerating the fine sugar or sugar alcohol crystals and the particles of crosslinked PVP.

The formulations according to the invention can advantageously also be used for the preparation of tablets, which are left to disintegrate in a glass of water prior to use. The preparation of tablets which are swallowed intact is of course also possible.

For the preparation of the tablets, the customary processes can be used, direct tabletting and roll compacting having particular advantages. Owing to the particular properties of the formulations according to the invention, as a rule only active substance, formulation according to the invention and a lubricant are required. The tablet formulation is therefore very simple and very reproducible and the process is easy to validate.

Surprisingly, it was found that a water-insoluble film-forming polymer considerably accelerates the disintegration of tablets. This is all the more surprising since such polymers are as a rule used for the preparation of retarded pharmaceutical dosage forms which do not disintegrate within several hours.

The disintegration times with the use of polyvinyl acetate as the water-insoluble polymer are considerably shorter than in the case of water-soluble polymers.

Furthermore, the formulations according to the invention have extremely good flowabilities and compressibilities, which lead to mechanically very stable tablets. The hardness of the tablets produced with the aid of the pharmaceutical formulations according to the invention is >50 N. Frequently, the hardnesses are above 80 N, even with the use of active substances which are difficult to press. The friabilities are <0.2%. There is therefore no damage during customary tablet handling.

Owing to the fine crosslinked polyvinylpyrrolidone, the tablets show virtually no changes in the tablet surface when stored under moist conditions. In contrast to coarse crosslinked polyvinylpyrrolidone, there is no pimple formation due to greatly swollen particles. The formulations according to the invention are therefore very stable during storage and retain their appealing appearance.

EXAMPLES

Examples A-H show the disintegration-promoting effect of polyvinyl acetate as the water-insoluble polymer compared with water-soluble polymers.

First, agglomerates were prepared in the fluidized bed: sugar/sugar alcohol and crosslinked PVP were initially taken and were agglomerated with aqueous binder solutions/dispersions, which were sprayed into the fluidized-bed granulator (from Glatt, GPCG 3.1) by means of the topspray method. Owing to its coarse particles, erythritol was first comminuted to a fine powder.

The preparation was effected by a two-stage agglomeration process, first a lower spray rate being chosen and then the spray rate being increased.

The following preparation conditions were used in a two-stage agglomeration process:

| | |
|---|---|
| Batch size: | 0.6 kg |
| Concentration of the binder solution/dispersion: | 10% by weight |
| Inlet air temperature: | 55° C. |
| Waste air temperature at the beginning: | 35° C. |
| Waste air temperature after changing the spray rate: | 25° C. |
| Spray rate at the beginning: | 7.5 g/min |
| Spray rate after change: | 20 g/min |

TABLE 1

Formulation composition of the agglomerates A to H in % by weight.

| | A | B | C | D | E | F | G | H |
|---|---|---|---|---|---|---|---|---|
| Lactose (Granulac 230) | 93 | 93 | — | — | — | — | — | — |
| Mannitol (Pearlitol 25 C) | — | — | 90 | 90 | 90 | 90 | 45 | 45 |
| Erythritol (Eridex 16952) | — | — | — | — | — | — | 45 | 45 |
| Crosslinked PVP (Kollidon CL) | 3.5 | 3.5 | 5.0 | 5.0 | 5.0 | 5.0 | 5.0 | 5.0 |
| PVP (Kollidon 30) | 3.5 | — | 5.0 | — | — | — | 5.0 | — |
| Polyvinyl alcohol/polyethylene glycol block copolymer (Kollicoat IR) | — | — | — | 5.0 | — | — | — | — |
| Methacrylic acid/ethyl acrylate copolymer (Kollicoat MAE 100 P) | — | — | — | — | 5.0 | — | — | — |
| Polyvinyl acetate | — | 3.5 | — | — | — | 5.0 | — | 5.0 |

The agglomerates thus prepared were mixed with from 0.5 to 1.0% by weight of lubricant (magnesium stearate) in a Turbula mixer for 5 min. These mixtures were then tabletted on a fully instrumented rotary tablet press (Korsch PH 100/6) at a speed of 30 rpm. The rotary tablet press was equipped with 6 punches (10 mm, biplanar, faceted). The tablet weight was adjusted to 300 mg. Thus, the tabletting was effected at a pressure of 18 KN (the tablet had different hardnesses depending on the compressibility of the powder), and the pressure was then adjusted in each case so that the hardness of the tablets was 60 N.

The tablets were investigated with regard to hardness (tablet tester HT-TMB-CI-12 from Kraemer), friability (Roche friabilator, Erweka) and disintegration time in phosphate buffer pH 7.2 (disintegration tester ZT 74, Erweka). The numerical data to the left of the oblique stroke relate to the tablets which were obtained using a pressure of 18 kN.

TABLE 2

Tablet properties for formulations A to H

| | Hardness [N] | Friability [%] | Disintegration time [s] |
|---|---|---|---|
| A | 180/60 | 0.10/0.15 | 120/75 |
| B | 180/60 | 0.05/0.15 | 45/20* |
| C | 200/60 | 0.15/0.20 | 180/120 |
| D | 250/60 | 0.15/0.25 | 210/150 |
| E | 220/60 | 0.10/0.25 | 240/180 |
| F | 200/60 | 0.02/0.15 | 60/20* |

TABLE 2-continued

Tablet properties for formulations A to H

|   | Hardness [N] | Friability [%] | Disintegration time [s] |
|---|---|---|---|
| G | 200/60 | 0.20/0.30 | 180/120 |
| H | 200/60 | 0.10/0.25 | 80/30 |

*Determination of disintegration times <20 s is not possible for reasons of end point detection.

Examples J to M show the suitability of a rapidly disintegrating excipient in an active substance formulation.

The rapidly disintegrating excipient is prepared by agglomerating mannitol (90% by weight) and crosslinked PVP (5% by weight) with polyvinyl acetate (5% by weight) in the fluidized bed. The direct tabletting agent thus prepared was mixed with active substance and from 0.5 to 1.0% by weight of lubricant (magnesium stearate) and then compressed on a rotary tablet press (Korsch PH 100/6) to give tablets having a hardness of 60 N.

TABLE 3

Active substance, amount of active substance, tablet weight and diameter of the active substance formulations J to M

|   | Active substance | Amount of active substance | Tablet weight | Diameter |
|---|---|---|---|---|
| J | Loratadine | 10 mg | 250 mg | 8 mm |
| K | Loperamide HCl | 2 mg | 100 mg | 6 mm |
| L | Cetirizine 2HCl | 10 mg | 280 mg | 10 mm |
| M | Lorazepam | 2 mg | 120 mg | 7 mm |

The tablets were investigated with regard to hardness (tablet tester HT-TMB-CI-12 F, from Kraemer), friability (Roche friabilator, Erweka) and disintegration time in phosphate buffer pH 7.2 (disintegration tester ZT 74, Erweka).

TABLE 4

Tablet properties for formulations J to M

|   | Hardness [N] | Friability [%] | Disintegration time [s] |
|---|---|---|---|
| J | 60 | <0.20 | 30 |
| K | 60 | <0.20 | 20* |
| L | 60 | <0.20 | 25 |
| M | 60 | <0.20 | 20* |

*Determination of disintegration times <20 s is not possible for reasons of end point detection

We claim:

1. A pharmaceutical formulation comprising agglomerates of:
   a) 60% to 97% by weight of sugar or sugar alcohols;
   b) 1% to 25% by weight of crosslinked polyvinylpyrrolidone;
   c) 1% to 15% by weight of water-insoluble, film-forming polymers;
   d) 0% to 15% by weight of water-soluble polymers; and
   e) 0% to 15% by weight of further pharmaceutically acceptable excipients, wherein the sum of a), b), c), d), and e) equals 100% by weight, and the mean particle size of said agglomerates is in the range of from 100 μm to 600 μm.

2. The formulation of claim 1, wherein said sugar alcohol is mannitol, erythritol, or mixtures thereof.

3. The formulation of claim 1, wherein said crosslinked polyvinylpyrrolidone comprises particles having a mean size of less than 50 μm.

4. The formulation of claim 1, wherein the hydration capacity of said crosslinked polyvinylpyrrolidone is greater than 6.5 g/g.

5. The formulation of claim 1, wherein said water-insoluble film-forming polymer is polyvinyl acetate.

6. The formulation of claim 1, wherein said water-insoluble film-forming polymer is polyvinyl acetate in the form of an aqueous dispersion.

7. The formulation of claim 1, wherein said water-soluble polymer is polyvinylpyrrolidone.

8. The formulation of claim 1, wherein said further pharmaceutically acceptable excipients are acidifying agents, sweeteners, flavors, flavor enhancers, colorants, thickeners, surfactants, and/or finely divided pigments.

9. The formulation of claim 1, comprising agglomerates of
   a) 70% to 95% by weight of sugar or sugar alcohols;
   b) 2% to 15% by weight of crosslinked polyvinylpyrrolidone;
   c) 1% to 10% by weight of water-insoluble, film-forming polymers;
   d) 0% to 2% by weight of water-soluble polyvinylpyrrolidone; and
   e) 0% to 15% by weight of further pharmaceutically acceptable excipients.

10. The formulation of claim 1, comprising agglomerates of
    a) 75% to 95% by weight of mannitol or erythritol or a mixture thereof;
    b) 3% to 10% by weight of crosslinked polyvinylpyrrolidone;
    c) 1% to 10% by weight of polyvinyl acetate;
    d) 0% to 2% by weight of water-soluble polyvinylpyrrolidone; and
    e) 0% to 15% by weight of further pharmaceutically acceptable excipients.

11. A tablet comprising the formulation of claim 1, said tablet having a disintegration time of less than 30 seconds in an aqueous medium.

12. The tablet of claim 11, wherein said tablet has a hardness greater than 50 N.

13. The tablet of claim 11, wherein said tablet comprises from 20% to 99% by weight, based on the total tablet weight, of the formulation of claim 1.

14. The tablet of claim 11, wherein said tablet comprises further excipients.

15. A process for preparing the formulation of claim 1 comprising agglomerating said sugar or sugar alcohol and said crosslinked polyvinylpyrrolidone with an aqueous dispersion of said water-insoluble, film-forming polymers, wherein said sugar or sugar alcohol comprises finely divided particles.

16. The process of claim 15, wherein said aqueous dispersion of the water-insoluble, film-forming polymers further comprises suspended crosslinked polyvinylpyrrolidone.

17. The process of claim 15, wherein said agglomeration is effected in a fluidized-bed granulator, a mixer, or a spray tower.

* * * * *